(12) United States Patent
Wright et al.

(10) Patent No.: US 10,882,180 B2
(45) Date of Patent: *Jan. 5, 2021

(54) ROBOTIC BASED HEALTH CARE SYSTEM

(71) Applicant: INTOUCH TECHNOLOGIES, INC., Goleta, CA (US)

(72) Inventors: Timothy C. Wright, Santa Barbara, CA (US); Fuji Lai, Goleta, CA (US); Marco Pinter, Santa Barbara, CA (US); Yulun Wang, Goleta, CA (US)

(73) Assignee: TELADOC HEALTH, INC., Purchase, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/679,697

(22) Filed: Nov. 11, 2019

(65) Prior Publication Data
US 2020/0215683 A1 Jul. 9, 2020

Related U.S. Application Data

(63) Continuation of application No. 13/432,365, filed on Mar. 28, 2012, now Pat. No. 10,471,588, which is a continuation of application No. 12/082,953, filed on Apr. 14, 2008, now Pat. No. 8,179,418.

(51) Int. Cl.
*A61B 34/00* (2016.01)
*B25J 9/00* (2006.01)
*B25J 19/02* (2006.01)
*G06Q 50/22* (2018.01)
*G06Q 50/24* (2012.01)
*B25J 9/16* (2006.01)
*G16H 10/60* (2018.01)
*G16H 40/63* (2018.01)

(52) U.S. Cl.
CPC .......... *B25J 9/0003* (2013.01); *B25J 9/1689* (2013.01); *B25J 19/023* (2013.01); *G06Q 50/22* (2013.01); *G06Q 50/24* (2013.01); *G16H 10/60* (2018.01); *G16H 40/63* (2018.01)

(58) Field of Classification Search
CPC .................................. H04B 17/00; B25J 5/00
USPC ....... 455/3.03, 419; 700/245, 259; 901/1, 47
See application file for complete search history.

(56) References Cited

U.S. PATENT DOCUMENTS

| 7,702,524 B1* | 4/2010 | Whibbs | G16H 10/60 |
| | | | 705/2 |
| 2008/0001774 A1* | 1/2008 | Huang | G08C 17/00 |
| | | | 340/13.24 |

* cited by examiner

*Primary Examiner* — George C Monikang

(57) ABSTRACT

A robotic system that can be used to treat a patient. The robotic system includes a mobile robot that has a camera. The mobile robot is controlled by a remote station that has a monitor. A physician can use the remote station to move the mobile robot into view of a patient. An image of the patient is transmitted from the robot camera to the remote station monitor. A medical personnel at the robot site can enter patient information into the system through a user interface. The patient information can be stored in a server. The physician can access the information from the remote station. The remote station may provide graphical user interfaces that display the patient information and provide both a medical tool and a patient management plan.

16 Claims, 8 Drawing Sheets

172  174  176

ADVANCED CONTROLS

| Start | Patient Info | NIHSS | t-PA | Summary |

170

Last Name: KANE    First Name: JESSAMINE

MRN: 3012296873    Age: 75

Gender: FEMALE    Weight: 50.50 Kgs

Patient History:    Heart Rate: 90

Diabetes ☐

178

3:00:00

HR    90
BP    120/80
NHSS    3

View Images

ADVANCED CONTROLS

| Start | Patient Info | NIHSS | t-PA | Summary |

MIH Stroke Scale:

Level of Consciousness: Please Select:

180

Please Select:
MOC Questions: 0 = Alert
1 = Not alert
LOC Commands: 2 = Not responsive Best Gaze: Please Select:

182

3:00:00

HR    84
BP    130/90
NHSS

View Images

ROBOTIC BASED HEALTH CARE SYSTEM

BACKGROUND OF THE INVENTION

1. Field of the Invention

The subject matter disclosed generally relates to the fields of health care and robotics.

2. Background Information

The increasing complexity of healthcare and resulting clinical specialization is causing fragmentation of care compromising patient safety and hospital efficiency. There is the need for availability of clinical specialist expertise to cut across time and space as well as the need for standardization and dissemination of best practices and protocols for optimal quality of care for citizens regardless of where they live.

The need for clinical specialist expertise is especially acute in the diagnosis, and treatment of stroke whereby immediate access to expertise and interdisciplinary communication and collaboration is key. Stroke is the second cause of death worldwide and the third leading cause of death in the United States. Recent development of several new therapies including tPA and neuro-endovascular procedures such as coiling offers real hope to change the once bleak prognosis for stroke victims. However, these new therapies are not widely available. Nationally, fewer than 5% of stroke victims are receiving any sort of treatment compared with leading stroke centers where approximately 25% of victims are treated. Most community hospitals do not have the basic patient assessment capability in place on a 24/7 basis nor have they established the appropriate ED treatment protocols. Additionally, only a very few hospitals have the specialists on staff required for neuro-endovascular procedures. Therefore stroke patients are either immediately transferred without proper evaluation or go untreated.

A major challenge in delivering stroke care relates to the time elements of stroke. The adage "time is brain" is often heard. The challenge is to get the right expertise and treatment to the patient at the right time. This encompasses the entire continuum of care from emergency medical services and ambulance transport to evaluation in the ED and definitive treatment. Some stroke care guidelines have been established by the National Institute for Neurological Disorders and Stroke (NINDS). For example, the guidelines suggest getting a patient with symptoms of stroke to stroke expertise (e.g. neurologist, stroke team activation) within fifteen minutes. The use of the word "expertise" here is significant in that the expert need not be physically present next to the patient but could be made available through a consult, for example, over the phone.

BRIEF SUMMARY OF THE INVENTION

A robotic system that includes a mobile robot that has a camera. The system also includes a user interface that allows medical information to be entered by a user. The mobile robot is coupled to a remote station that can control movement of the robot. The remote station includes a monitor that is coupled to the mobile robot camera and displays the medical information.

BRIEF DESCRIPTION OF THE DRAWINGS

FIG. 6 is a graphical user interface at the remote station;
FIG. 7 is a graphical user interface when a NIHSS tab is selected;
FIG. 9 is a graphical user interface displayed when a view images button is selected.

DETAILED DESCRIPTION

Disclosed is a robotic system that can be used to treat a patient. The robotic system includes a mobile robot that has a camera. The mobile robot is controlled by a remote station that has a monitor. A physician can use the remote station to move the mobile robot into view of a patient. An image of the patient is transmitted from the robot camera to the remote station monitor. A medical personnel at the robot site can enter patient information into the system through a user interface. The patient information can stored in a server. The physician can access the information from the remote station. The remote station may provide graphical user interfaces that display the patient information and provide a medical tool. By way of example, the remote station may present to the user a NIHSS questionnaire to determine the severity of a stroke. The graphical user interfaces may include an interface that provides a patient management plan such as a calculated dosage. The medical tool and dosage can be transmitted to the user interface so that this information can be viewed by medical personnel in physical proximity to the patient. The system allows a clinical specialist to remotely observe and treat a patient. This is particularly advantageous when treating stroke patients, where time is critical.

Figure 1:
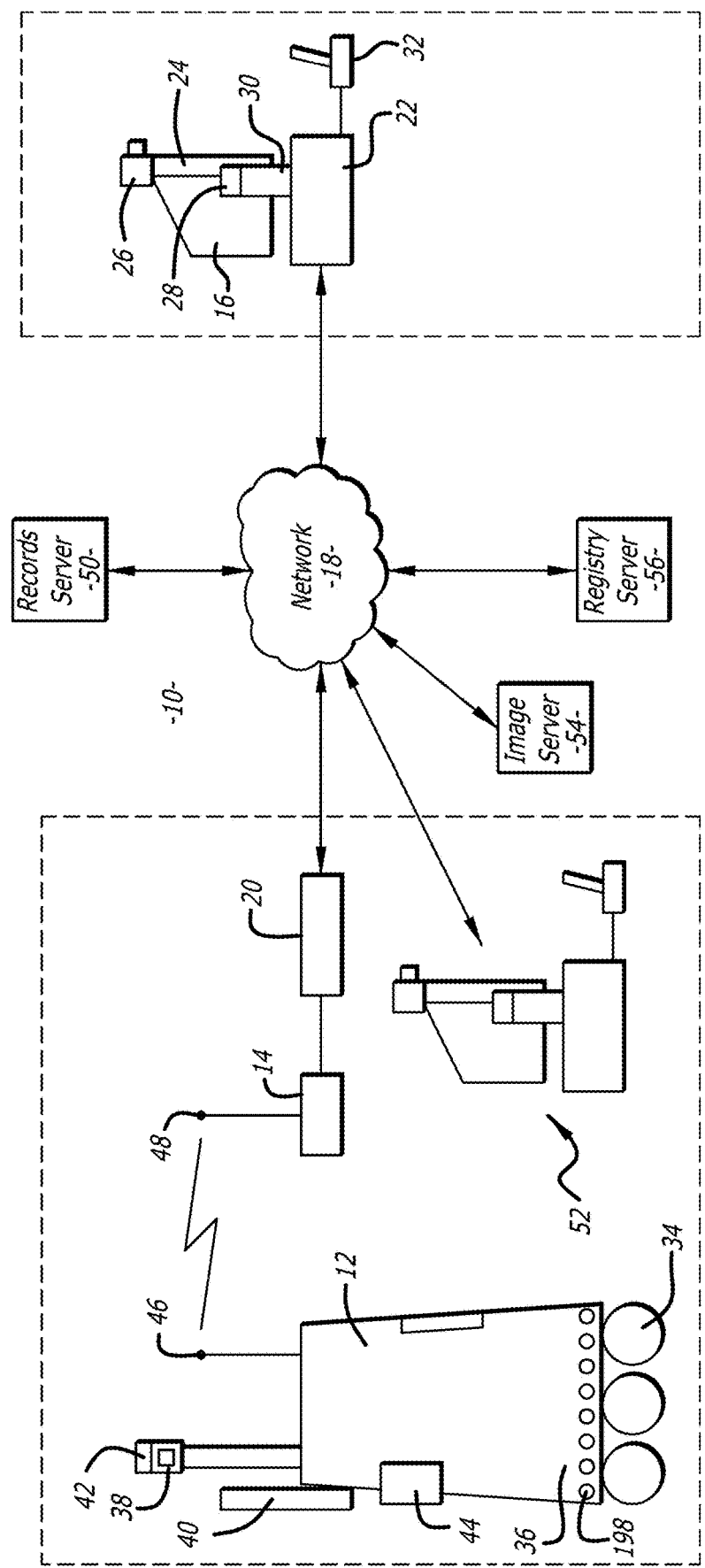
FIG. 1 is an illustration of a robotic system.

Referring to the drawings more particularly by reference numbers, FIG. 1 shows a robotic system 10. The robotic system 10 includes one or more robots 12. Each robot 12 has a base station 14. The robot 12 is coupled to a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. The robot 12 may also have a camera 38, a monitor 40, a microphone(s) 42 and a speaker(s) 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through operation of the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The system 10 may include a records server 50 that can be accessed through the network 18. Patient information can be provided to the server 50 through a user interface 52. The user interface 52 may or may not be in close proximity to the robot 12. For example, the user interface may be a computer located at a nurses station where information is entered when a patient checks into a facility. The robot 12 can be moved into view of the patient so that patient information can be entered into the system while a physician is viewing the patient through the robot camera. The physician can remotely move the robot to obtain different viewing angles of the patient. The user interface 52 may be a separate computer terminal. Alternatively, the user interface 52 may be integral with the robot. For example, the robot monitor may be a touch screen that allows a user to enter data into the system through the robot 12. The server 50 may contain other medical records of a patient such as written records of treatment, patient history, medication information, x-rays, EKGs, laboratory results, physician notes, etc.

The system 10 may also include an image server 54 and a registry server 56. The image server 54 may include medical images. For example, the medical images may include CT scans of a patient's brain. The images can be downloaded to one of the remote stations 14 through the network 18. The registry server 56 may store historical data on patients. The historical data can be downloaded to a remote computer 16 through the network 18.

Figure 2:
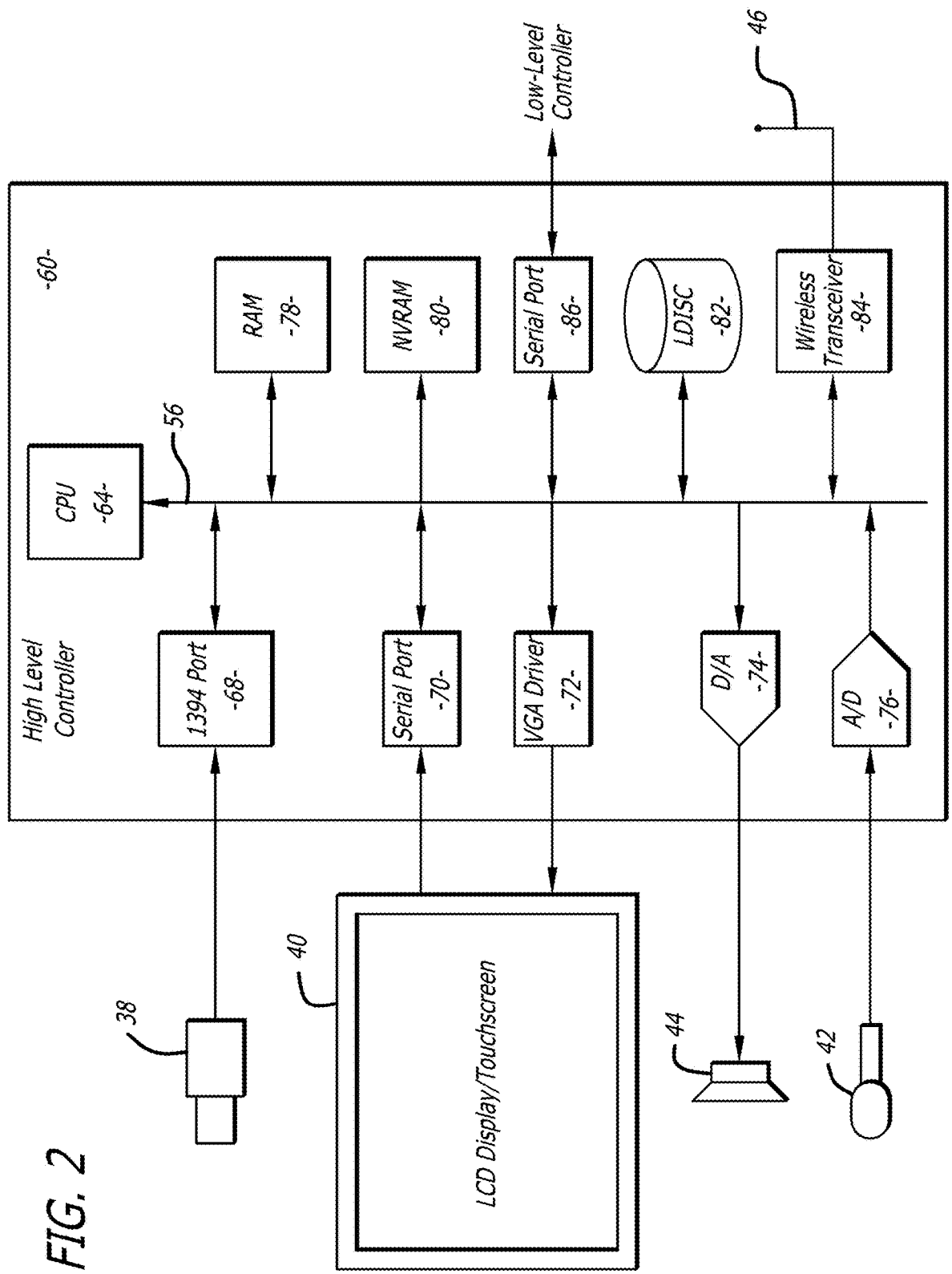
FIG. 2 is a schematic of an electrical system of a robot.
Figure 3:
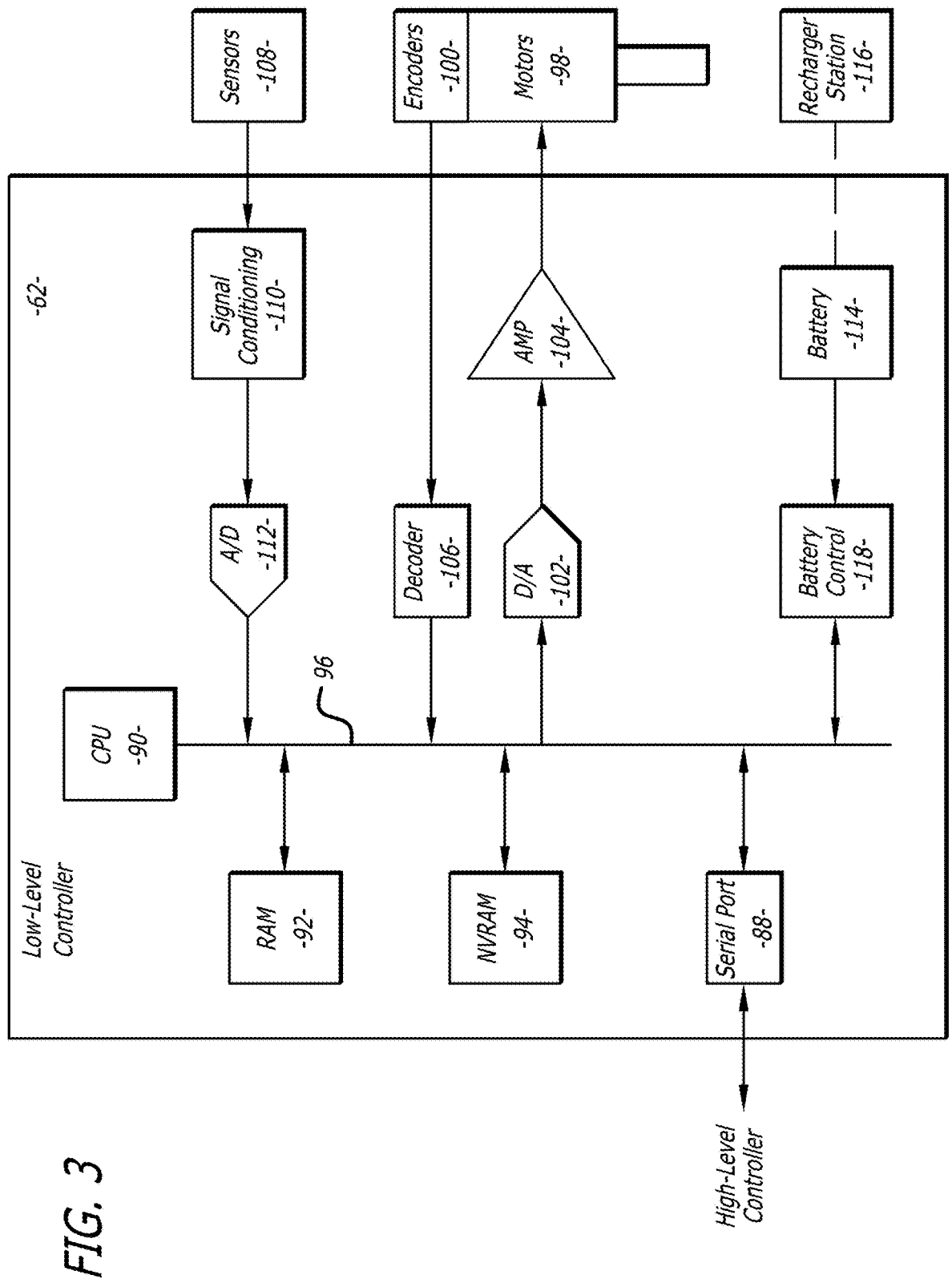
FIG. 3 is a further schematic of the electrical system of the robot.

FIGS. 2 and 3 show an embodiment of a robot 12. Each robot 12 may include a high level control system 60 and a low level control system 62. The high level control system 60 may include a processor 64 that is connected to a bus 66. The bus is coupled to the camera 38 by an input/output (I/O) port 68, and to the monitor 40 by a serial output port 70 and a VGA driver 72. The monitor 40 may include a touchscreen function that allows a user to enter input by touching the monitor screen.

The speaker 44 is coupled to the bus 56 by a digital to analog converter 74. The microphone 42 is coupled to the bus 66 by an analog to digital converter 76. The high level controller 60 may also contain random access memory (RAM) device 78, a non-volatile RAM device 80 and a mass storage device 82 that are all coupled to the bus 72. The mass storage device 82 may contain medical files of the patient that can be accessed by the user at the remote control station 16. For example, the mass storage device 82 may contain a picture of the patient. The user, particularly a health care provider, can recall the old picture and make a side by side comparison on the monitor 24 with a present video image of the patient provided by the camera 38. The robot antennae 46 may be coupled to a wireless transceiver 84. By way of example, the transceiver 84 may transmit and receive information in accordance with IEEE 802.11b.

The controller 64 may operate with a LINUX OS operating system. The controller 64 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 60 operates to control communication between the robot 12 and the remote control station 16.

The high level controller 60 may be linked to the low level controller 62 by a serial port 88. The low level controller 62 includes a processor 90 that is coupled to a RAM device 92 and non-volatile RAM device 94 by a bus 96. Each robot 12 contains a plurality of motors 98 and motor encoders 100. The encoders 100 provide feedback information regarding the output of the motors 98. The motors 98 can be coupled to the bus 96 by a digital to analog converter 102 and a driver amplifier 104. The encoders 100 can be coupled to the bus 86 by a decoder 106. Each robot 12 may have a number of proximity sensors 108 (see also FIG. 1). The sensors 108 can be coupled to the bus 96 by a signal conditioning circuit 110 and an analog to digital converter 112.

The low level controller 62 runs software routines that mechanically actuate the robot 12. For example, the low level controller 62 provides instructions to actuate the movement platform to move the robot 12. The low level controller 62 may receive movement instructions from the high level controller 60. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 114. The battery 114 may be recharged by a battery recharger station 116 (see also FIG. 1). The low level controller 62 may include a battery control circuit 118 that senses the power level of the battery 114. The low level controller 62 can sense when the power falls below a threshold and then send a message to the high level controller 60.

The system may be the same or similar to a robotic system provided by the assignee InTouch Technology, Inc. of Santa Barbara, Calif. under the name RP-7, which is hereby incorporated by reference. The system may also be the same or similar to the system disclosed in U.S. Pat. No. 7,292,912, which is hereby incorporated by reference.

Figure 4:
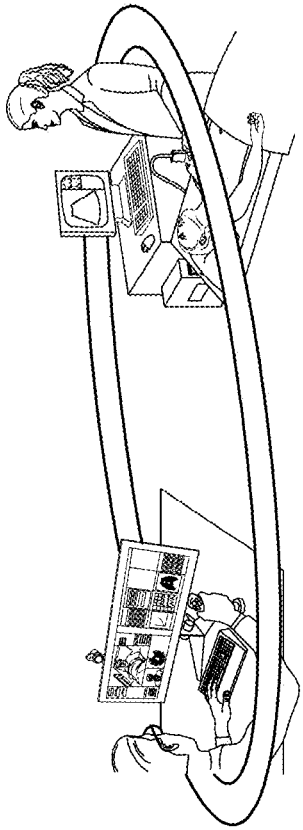
FIG. 4 is a graphical user interface of a user interface.

FIG. 4 shows a graphical user interface 150 provided at the user interface 52. The graphical user interface 150 includes a plurality of data fields 152 that can be filled by the user. The data fields 152 can request patient information such as name, age, etc. The data fields may also include request for medical data such as heart rate, glucose level and blood pressure ("SBP" and "DBP").

Figure 5:
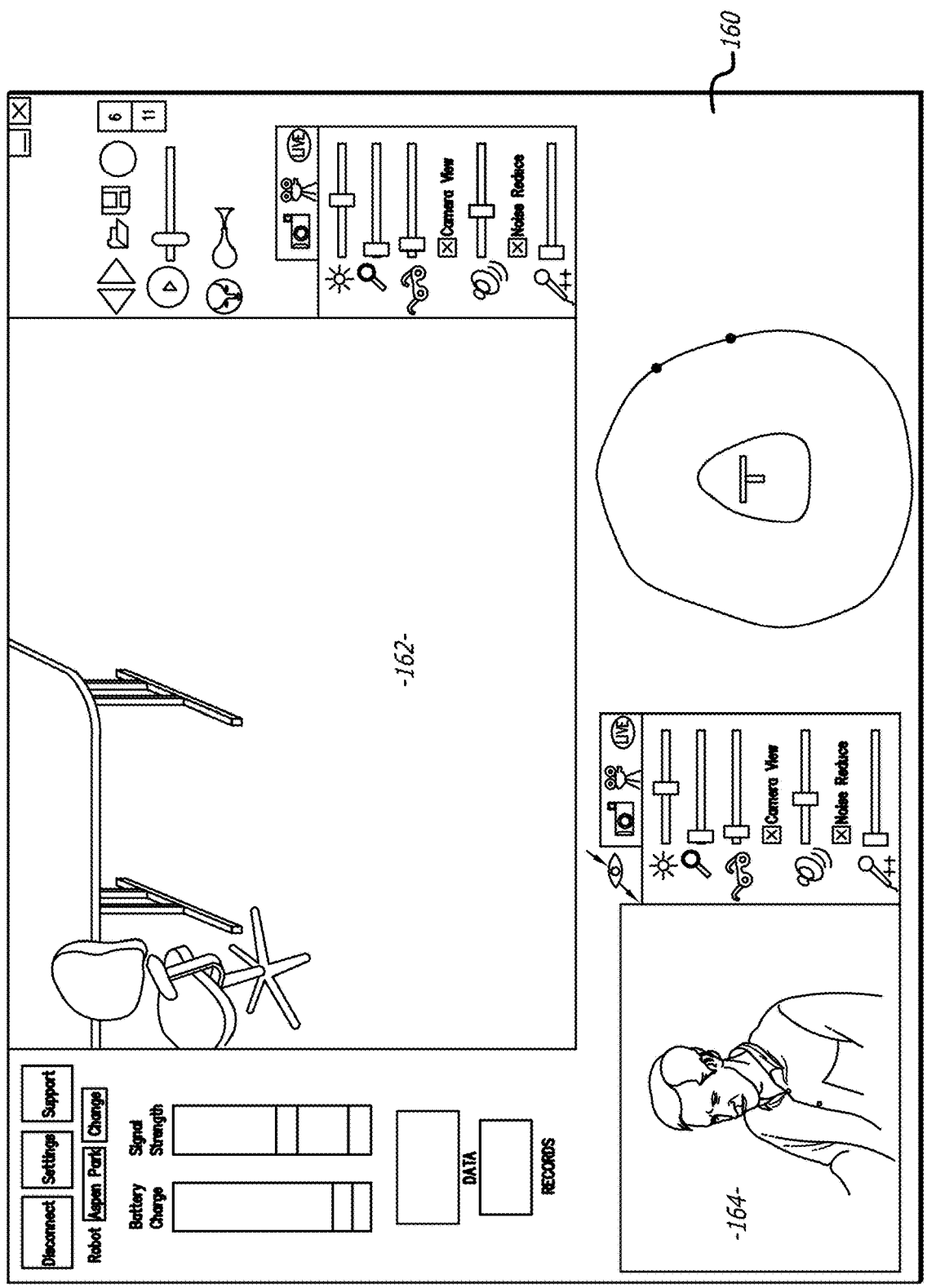
FIG. 5 is a graphical user interface at a remote station.

FIG. 5 shows a display user interface ("DUI") 160 that can be displayed at the remote station 14. The DUI 160 may include a robot view field 162 that displays a video image captured by the camera of the robot. The DUI 160 may also include a station view field 164 that displays a video image provided by the camera of the remote station 14. The DUI 160 may be part of an application program stored and operated by the computer 22 of the remote station 14.

FIG. 6 shows a graphical user interface 170 that is displayed by the monitor of the remote station 16. The interface 170 includes a "PATIENT INFO" tab 172, a "NIHSS" tab 174 and a "t-PA" tab 176. Selection of the PATIENT INFO tab 172 displays various data fields 178 including patient name, age, weight, heart rate, etc. This may be the same information through the user interface.

FIG. 7 shows an interface 180 when the "NIHSS" tab 174 is selected. The interface 180 has a data field 182 that provides a questionnaire to rate the severity of a stroke victim using the NIHSS stroke scale. This provides a readily available medical tool for the physician.

Figure 8:
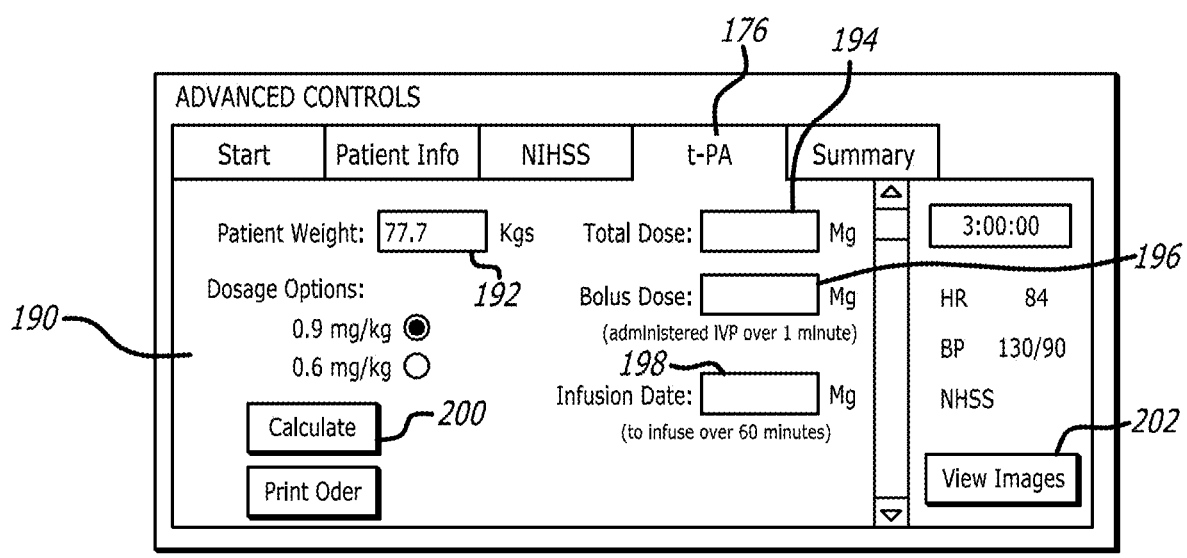
FIG. 8 is a graphical user interface displayed when a t-PA table is selected
Figure 9:
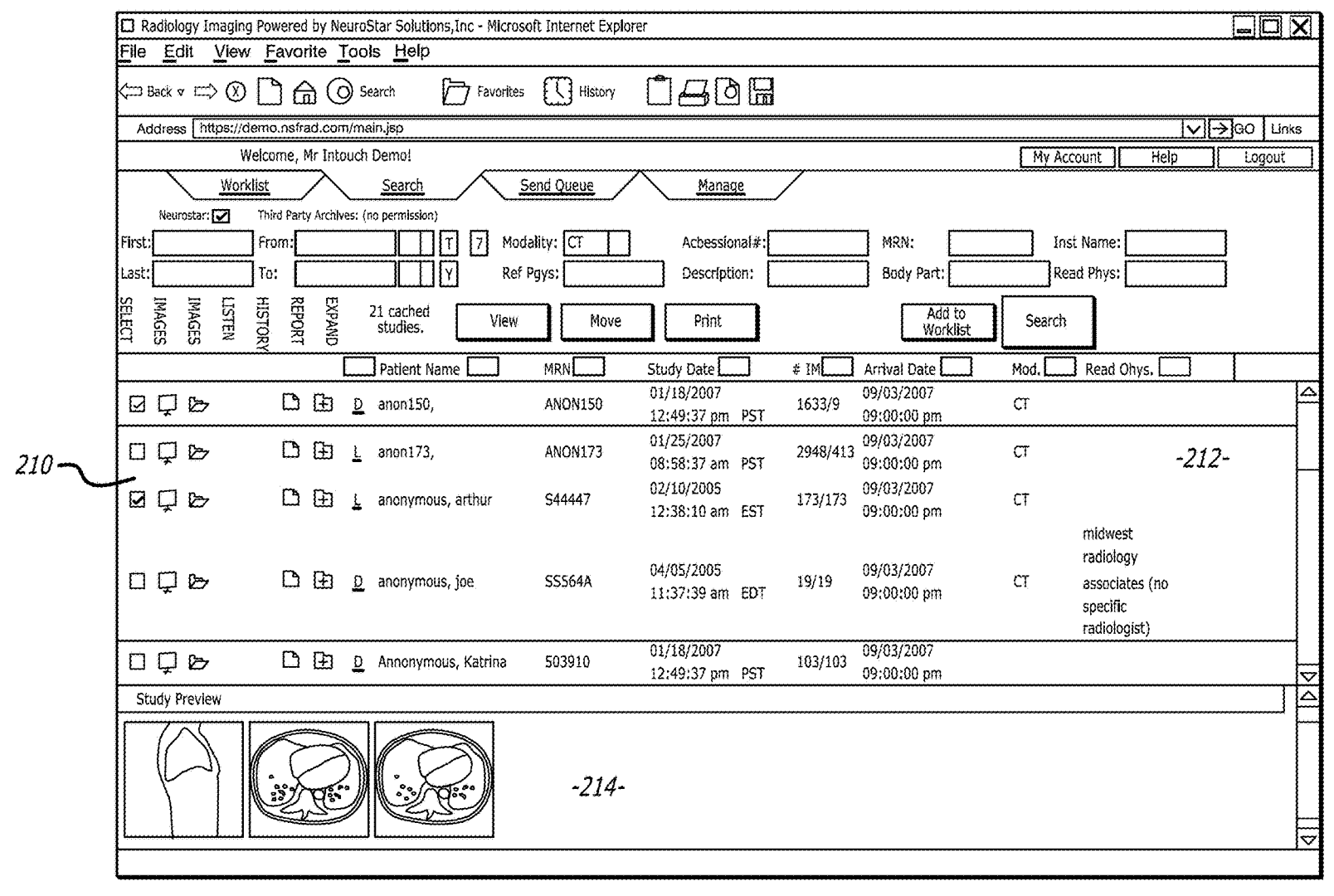

FIG. 8 shows an interface 190 when the "t-PA" tab 176 is selected. The interface 190 may include a data field 192 that provides the patient's weight, a "TOTAL DOSE" data field 194, a "BOLUS DOSE" data field 196 and an "INFUSION DOSE" data field 198. The interface 190 may also include a "CALCULATE" button 200. When the CALCULATE button 182 is selected the data fields 194, 196 and 198 are automatically populated with a calculated dosage. This provides a patient management plan for the physician to review. The interfaces 170, 180 and 190 also have a "VIEW IMAGES" button 202 that when selected displays an interface 210 shown in FIG. 9. The interface 210 includes a data field 212 and an image field 214. The image field 214 can provide a plurality of medical images such as a CT scan of the patient's head.

The system is useful for allowing a physician to remotely view and treat a stroke patient. The system provides patient information, NIHSS stroke severity assessment, calculated t-PA dosage and CT head images that allow the physician to provide real time remote patient treatment.

While certain exemplary embodiments have been described and shown in the accompanying drawings, it is to be understood that such embodiments are merely illustrative of and not restrictive on the broad invention, and that this invention not be limited to the specific construction's and arrangements shown and described, since various other modifications may occur to those ordinarily skilled in the art.

What is claimed is:

1. A robotic system, comprising:
 a network;
 a telepresence device in the vicinity of a patient and coupled to the network, the telepresence device having a camera, a monitor, a microphone, and a speaker, the telepresence device camera captures an image of the patient;
 a computer at a nurses station that displays a user interface, the user interface allows medical information to be entered by displaying a plurality of data fields that include at least one patient information field and at least one medical data field that are filled by a user at the computer, the computer is separate from the telepresence device and is coupled to the network independently of the telepresence device; and,
 a remote station located remotely from both the telepresence device and the computer at the nurses station, the remote station is coupled to said telepresence device via the network and controls the telepresence device, the remote station includes a monitor that displays a user interface including the image of the patient, the patient information, and the medical data provided by the user at the computer at the nurses station.

2. The system of claim 1, further comprising a records server that is coupled to the remote station and the nurses computer and stores the medical information.

3. The system of claim 1, further comprising an image server that is coupled to the remote station and stores a plurality of medical images.

4. The system of 1, wherein the medical information includes patient statistics.

5. The system of claim 1, wherein the remote station provides a medical tool.

6. The system of claim 5, wherein the medical tool is a stroke evaluation.

7. The system of 1, wherein the user interface can receive information from an input device of the remote station.

8. The system of claim 1, wherein the user interface displays a patient management plan.

9. A method for providing a remote medical consultation, the method comprising:
 capturing an image of a patient with a telepresence device that is coupled to a network and includes a camera, a monitor, a microphone, and a speaker;
 displaying a plurality of data fields on a user interface of a computer at a nurses station, the computer is separate from the telepresence device and is coupled to the network independently of the telepresence device;
 receiving medical information from a user at the nurses station computer, the medical information including at least one patient information field and at least one medical data field that are filled by the user;
 controlling the telepresence device via a remote station that is coupled to the network; and
 displaying, on a monitor of the remote station, a user interface including the image of the patient, the patient information, and the medical data provided by the user at the computer at the nurses station.

10. The method of claim 9, further comprising storing the medical information at a records server that is coupled to the network.

11. The method of claim 9, further comprising storing a plurality of medical images at an image server that is coupled to the remote station.

12. The method of 9, wherein the medical information includes patient statistics.

13. The method of claim 9, further comprising providing a medical tool via the remote station.

14. The method of claim 13, wherein the medical tool is a stroke evaluation.

15. The method of claim 9, further comprising receiving information from an input device of the remote station.

16. The method of claim 9, further comprising displaying a patient management plan at the remote station.

* * * * *